United States Patent
Saka

(10) Patent No.: US 7,227,030 B2
(45) Date of Patent: Jun. 5, 2007

(54) METHOD FOR PRODUCING FATTY ACID ALKYL ESTER COMPOSITION

(76) Inventor: Shiro Saka, 33-14, Konooka-cho, Otsu-shi, Shiga (JP) 520-0103

( * ) Notice: Subject to any disclaimer, the term of this patent is extended or adjusted under 35 U.S.C. 154(b) by 0 days.

(21) Appl. No.: 10/517,485

(22) PCT Filed: Jun. 12, 2003

(86) PCT No.: PCT/JP03/07492

§ 371 (c)(1),
(2), (4) Date: Jul. 6, 2005

(87) PCT Pub. No.: WO03/106604

PCT Pub. Date: Dec. 24, 2003

(65) Prior Publication Data

US 2006/0025620 A1    Feb. 2, 2006

(30) Foreign Application Priority Data

Jun. 13, 2002    (JP)    ............................... 2002-173225

(51) Int. Cl.
*C07C 51/00*    (2006.01)
(52) U.S. Cl. .................................................. 554/169
(58) Field of Classification Search ................ 554/169
See application file for complete search history.

(56) References Cited

U.S. PATENT DOCUMENTS 6,288,251 B1    9/2001    Tsuto et al.

FOREIGN PATENT DOCUMENTS

| EP | 1 061 120 A1 | 12/2000 |
|----|--------------|---------|
| EP | 001061120 A1 * | 12/2000 |
| JP | 2000-204392 | 7/2000 |

OTHER PUBLICATIONS

Hiroyuki Yoshida and Kei Makino, The Society of Chemical Engineers, 34 Ed., p. 278, *Conversion of Fish Oil to Bio-Diesel Fuel with Supercritical Methanol*, Aug. 31, 2001 (Full English Translation).

* cited by examiner

*Primary Examiner*—Deborah D. Carr
(74) *Attorney, Agent, or Firm*—Roberts Mlotkowski & Hobbes; Thomas W. Cole

(57) ABSTRACT

An object of the present invention is to solve a problem of separation and recovery of catalysts present in an alkali metal catalytic method currently often used, a problem of excess consumption of a catalyst by a free fatty acid in a raw material, and other problems, and to solve a problem of the presence of a large excess amount of alcohol in a conventional supercritical methanol method, and to provide a method for producing a fatty acid alkyl ester composition in a reaction system containing water and free fatty acid present. The present invention has attained the above-mentioned object by provided a method for producing a fatty acid alkyl ester composition using fats and oils containing a fatty acid glyceride and/or fatty acid, wherein alcohol and/or water is allowed to co-exist with the above-mentioned fats and oils and the reaction is conducted under conditions of a temperature of 100° C. to 370° C. and a pressure of 1 to 100 MPa.

9 Claims, 6 Drawing Sheets

Comparison of esterification reaction of fatty acid and transesterification of fatty acid glyceride in supercritical alcohol treatments at 300°C and 30 Mpa F I G. 1
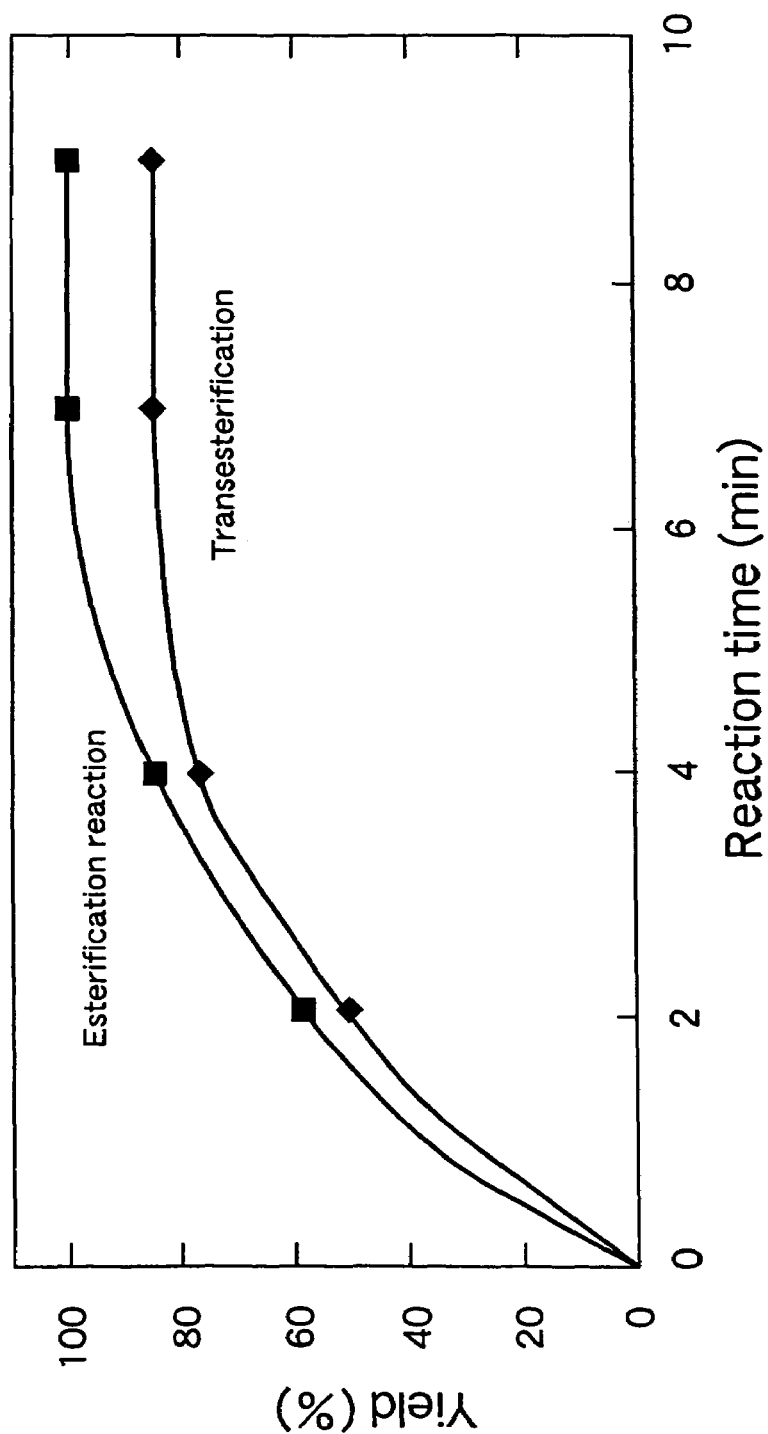

F I G. 2
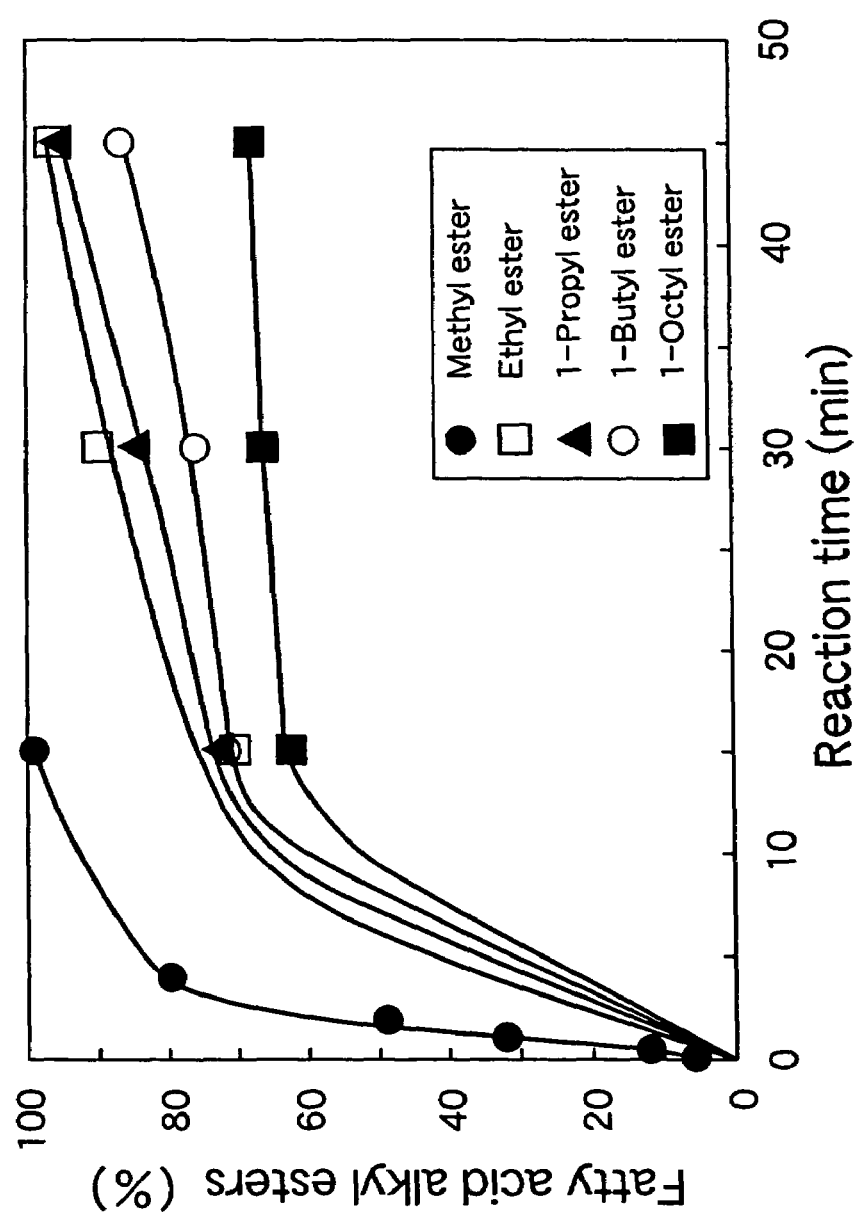

F I G. 3
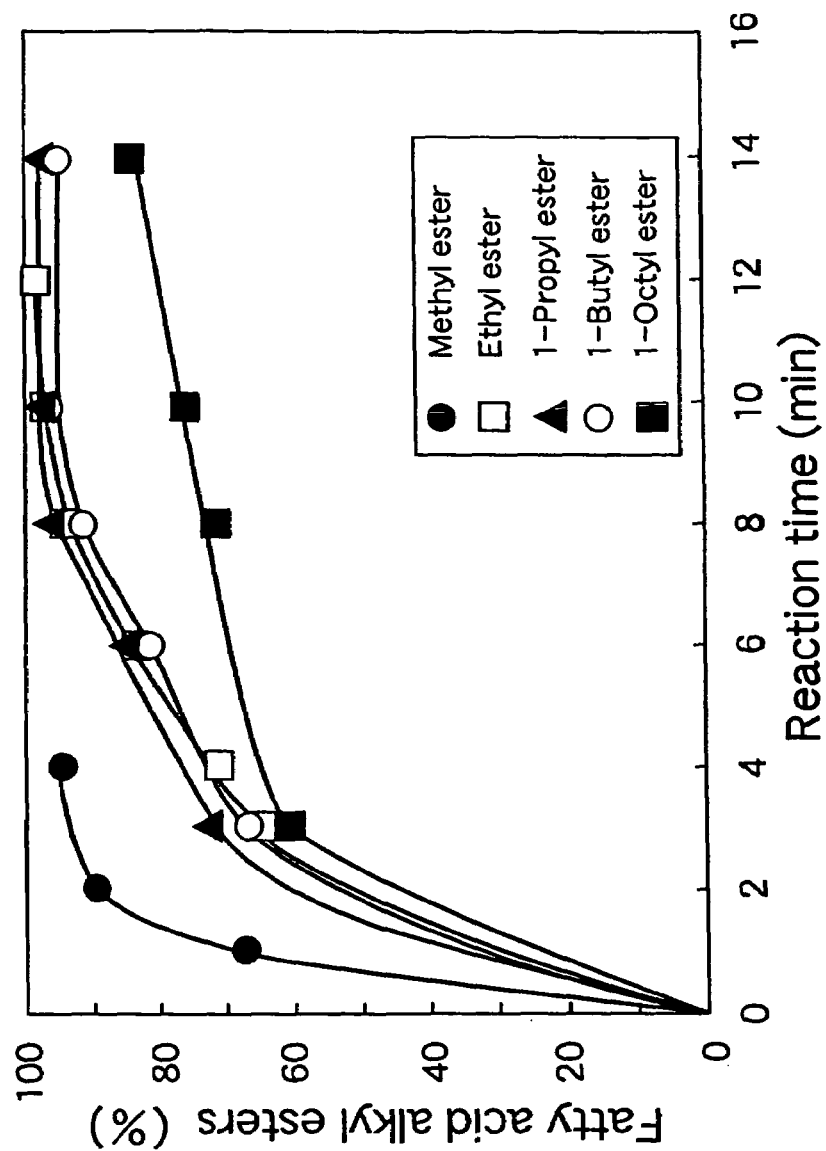

METHOD FOR PRODUCING FATTY ACID ALKYL ESTER COMPOSITION

TECHNICAL FIELD

The present invention relates to a method for producing fatty acid alkyl ester composition capable of being utilized effectively as a diesel fuel (particularly, bio-diesel fuel) by treating fats and oils containing a fatty acid glyceride and/or fatty acid, more specifically, to a method for solving a problem of separation and recovery of catalysts present in an alkali metal catalytic method currently often used, a problem of excess consumption of a catalyst by a free fatty acid in a raw material, and a problem of solving a decrease in reactivity due to water in a raw material and using a large excess amount of alcohol in a conventional supercritical methanol method, and producing a fatty acid alkyl ester composition at high yield in a reaction system containing water and free fatty acid present.

BACKGROUND ART

It has been long known that a fatty acid alkyl ester is obtained by transesterification of an alkyl alcohol with a mono-glyceride, di-glyceride and tri-glyceride (these are generically called fatty acid glyceride) which are main components of vegetable oils, animal fats and used fats and oils of them (for example, "Organic Chemistry Handbook," Gihodo Publication, 1988, pp. 1407 to 1409). Furthermore, various investigations have been made on a technology of producing a fatty acid alkyl ester which can be used as a diesel fuel from fats and oils, utilizing this reaction.

As a method for industrially producing a fatty ester from a fatty acid glyceride, there are long known methods in which a fatty acid glyceride is once hydrolyzed to be converted into a fatty acid, then, in the presence of an acid catalyst or enzyme catalyst, the fatty acid is further subjected to a dehydration reaction (esterification reaction) with alcohols under an anhydrous condition to be converted into a fatty acid alkyl ester, however, these are scarcely used as an industrial production method due to low reaction rate. Currently, in industrially often used methods, a fatty tri-glyceride is subjected to a transesterification under an anhydrous condition in the presence of an alkali metal catalyst under normal pressure at ambient temperature or temperatures near the boiling point of an alcohol with shorter alkyl chain. However, since, in this reaction, an alkali metal catalyst is dissolved in the reaction solution, there is a problem that the alkali metal catalyst is dissolved in a solution of the product and separation and recovery thereof are difficult.

Further, waste oils and the like often contain water, consequently, removal of water in a raw material is inevitable as a pre-treatment, in use of the above-mentioned alkali metal catalyst method. It is general that natural fats and oils contain a free fatty acid, and the content of a free fatty acid differs depending on the origin of a raw material and its treatment method. For example, a waste edible oil contains 3% or more of fatty acids and palm oil from an oil pressing process contains 5% or more of fatty acids. When an alkali metal catalyst is used under a condition of inclusion of a large amount of free fatty acids, an alkali soap becomes a by-product and an alkali metal catalyst in an excess amount is necessary, alternatively, there occurs a problem that separation of a fatty acid ester layer and a glycerin layer is difficult due to a by-product alkali soap, and the like. Because of these reasons, when a transesterification of a fatty acid glyceride is conducted in the presence of an alkali metal catalyst, a pre-treatment process is necessary for removing a free fatty acid.

From the standpoint of avoiding such a problem, for example, Japanese Published Unexamined Patent Application No. S61-14044 discloses also a method of converting into an ester of a free fatty acid with the aid of an acid catalyst, as a pre-treatment process. In this method, a free fatty acid is converted into an ester as a pre-treatment for conducting a transesterification of a fatty acid glyceride in the presence of an alkali metal catalyst, however, there is a problem that removal of an acid catalyst is necessary before performing the next transesterification of a fatty acid glyceride and when an acid catalyst remains, it is neutralized, consequently, the use amount of an alkali metal catalyst increases corresponding to the neutralization amount.

As a method for producing a fatty ester not requiring the above-mentioned pre-treatment process, there are also suggested methods using a solid acid catalyst (for example, Japanese Published Unexamined Patent Application No. H6-313188). However, an acid catalyst has a critical defect that the reactivity thereof for a transesterification of fats and oils is lower as compared with that of an alkali metal catalyst, and there is a problem that a large amount of catalyst is necessary in a transesterification using an acid catalyst.

On the other hand, there are recently also suggested so-called supercritical methanol methods in which a transesterification of fats and oils is conducted under supercritical conditions for alcohol without using a catalyst (for example, Japanese Published Unexamined Patent Application No. 2000-204392, 2000-109883). However, in the supercritical methanol method, there is a disadvantage that a large excess amount of alcohol should be present and higher temperatures of 300° C. or more are necessary, for efficient progress of a transesterification. Further, in this method, an effect of the presence of water in the reaction system has not been confirmed.

The present invention has been made notifying such conditions, and an object thereof is to solve a problem of separation and recovery of catalysts present in an alkali metal catalytic method currently often used, a problem of excess consumption of a catalyst by a free fatty acid in a raw material, and a problem of decrease in transesterification due to water in a raw material and to solve a problem of the presence of a large excess amount of alcohol in a conventional supercritical methanol method, and the present invention provides a method for producing a fatty acid alkyl ester, that is effective for conversion into a fatty acid alkyl ester from raw material oils which cannot be treated by conventional technologies such as a dark oil containing a free fatty acid as a main component discharged particularly from a purification process in an oil production factory, and a waste edible oil having a high free fatty acid content and/or water content, and the like.

DISCLOSURE OF THE INVENTION

The present inventors have intensively studied and resultantly found that the above-mentioned problems can be solved by conducting a reaction under specific conditions in the co-existence of alcohol and/or water with fats and oils, in producing a fatty acid alkyl ester composition using fats and oils containing a fatty acid glyceride and/or fatty acid.

The present invention has been made based on the above-mentioned finding, and provides a method for producing a fatty acid alkyl ester composition using fats and oils containing a fatty acid glyceride and/or fatty acid, wherein alcohol and/or water is allowed to co-exist with the above-mentioned fats and oils and the reaction is conducted under conditions of a temperature of 100° C. to 370° C. and a pressure of 1 to 100 MPa.

In this specification, "fats and oils" means those containing a fatty acid glyceride and/or fatty acid as described above and containing as a main component a generally called fatty acid mono-glyceride, fatty acid di-glyceride or fatty acid tri-glyceride, and additionally, means a fatty acid, and a mixture thereof. Namely, "fats and oils" also include widely those containing no fatty acid glyceride and containing only a fatty acid.

BRIEF DESCRIPTION OF THE DRAWINGS

FIG. 1 is a graph showing a difference in the relation between the reaction time and the yield of a methyl ester composition in an esterification reaction of a fatty acid and a transesterification of a fatty acid glyceride by supercritical methanol treatment at 300° C. and 30 Mpa.

FIG. 2 is a graph showing a difference in the relation between the reaction time of a transesterification of rapeseed oil by various supercritical alcohol treatments at 300° C. and the yield of the produced various fatty acid alkyl ester compositions. The alcohols used are methyl alcohol, ethyl alcohol, 1-propyl alcohol, 1-butyl alcohol and 1-octyl alcohol.

FIG. 3 is a graph showing a difference in the relation between the reaction time of a transesterification of rapeseed oil by various supercritical alcohol treatments at 350° C. and the yield of the produced various fatty acid alkyl ester compositions.

BEST MODES FOR CARRYING OUT THE INVENTION

Figure 4:
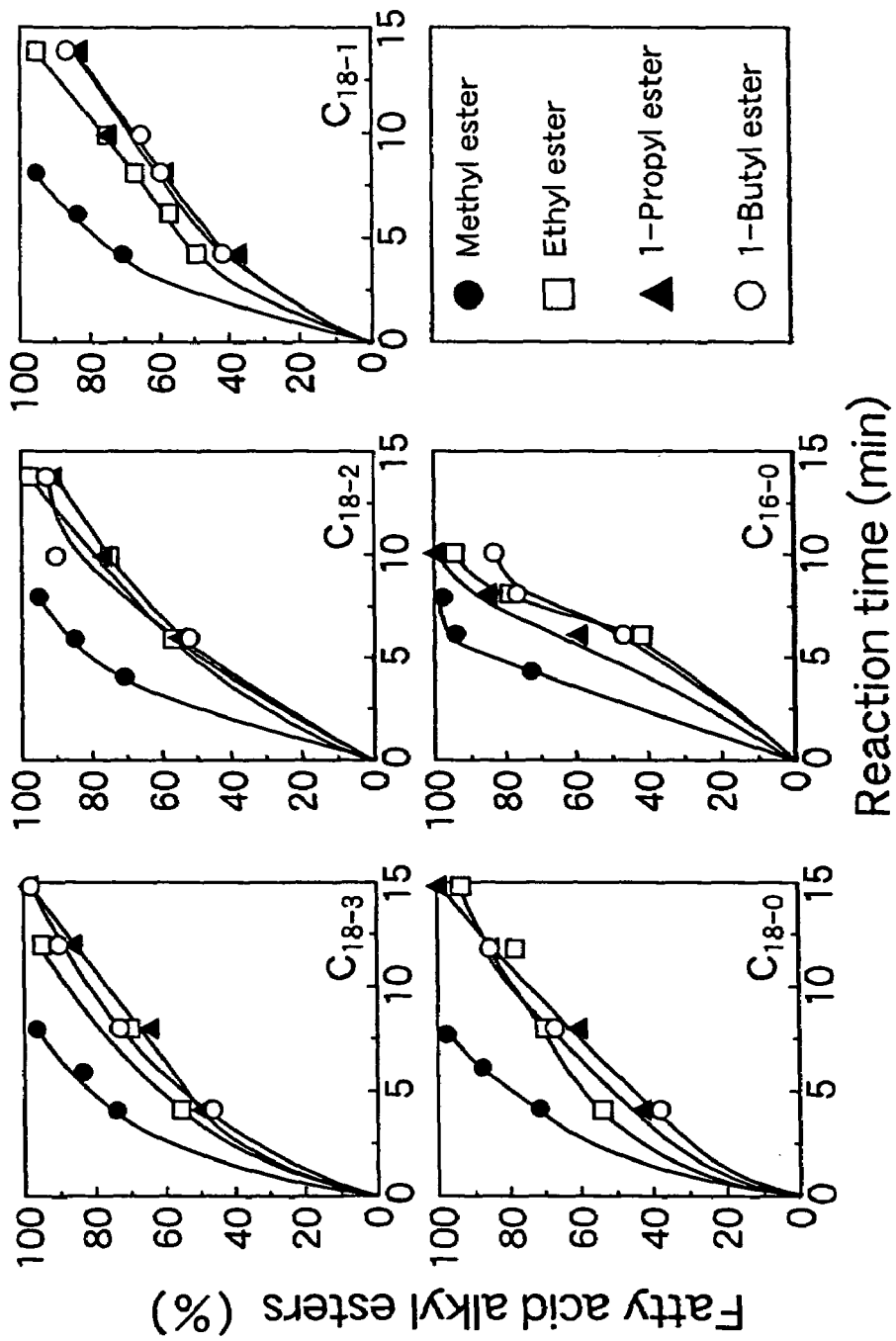
FIG. 4 provides graphs showing a difference in the relation between the reaction time of an esterification reaction of various fatty acids by various supercritical alcohol treatments at 300° C. and the yield of the produced various fatty acid alkyl ester compositions.

The method for producing a fatty acid alkyl ester composition of the present invention will be illustrated in detail based on its preferable embodiments.

The production method of the present invention is a method for producing a fatty acid alkyl ester composition using fats and oils containing a fatty acid glyceride and/or fatty acid, wherein alcohol and/or water is allowed to co-exist with the above-mentioned fats and oils and the reaction is conducted under conditions of a temperature of 100° C. to 370° C. and a pressure of 1 to 100 MPa.

Because of such a constitution, the method of the present invention does not cause a problem of separation and recovery of catalysts present in an alkali metal catalytic method, a problem of excess consumption of a catalyst by a free fatty acid in a raw material, and a problem of a decrease in transesterification due to water in a raw material, and further, solves a problem of the presence of a large excess amount of alcohol in a conventional supercritical methanol method, and enables production of a fatty acid alkyl ester composition at a high yield even in the reaction system containing water and free fatty acid present. Further, the method of the present invention is effective for conversion into a fatty acid alkyl ester from raw material oils which cannot be treated by conventional technologies such as a dark oil containing a free fatty acid as a main component discharged particularly from a purification process in an oil production factory, and a waste edible oil having a high free fatty acid content and/or water content, and the like.

In the production method of the present invention, the kind of reaction conducted and the number of steps of the reaction process are not particularly restricted provided that alcohol and/or water is allowed to co-exist with the above-mentioned fats and oils and the reaction is conducted under conditions of a temperature of 100° C. to 370° C. and a pressure of 1 to 100 MPa.

(First Embodiment)

The present invention preferably comprises a process in which alcohol and/or water is allowed to co-exist with the above-mentioned fats and oils containing at least a fatty acid glyceride, and the reaction is conducted under conditions of a temperature of 100 to 370° C. and a pressure of 5 to 100 MPa (preferably 5 to 50 MPa), to convert a fatty acid glyceride and fatty acid contained in the above-mentioned fats and oils into a fatty acid alkyl ester (first embodiment). According to such a first embodiment, water and alcohol, in particular water, works as an acid catalyst, a fatty acid glyceride reacts with alcohol by a transesterification, to give a fatty acid alkyl ester. A part of a fatty acid glyceride is hydrolyzed with water to give a fatty acid, however, since an esterification reaction progresses utilizing water and alcohol, particularly water as an acid catalyst to give a fatty acid alkyl ester, the co-existence of water with alcohol is useful.

In the first embodiment, to conduct the reaction under reaction conditions of, particularly, a temperature of 200 to 300° C. and a pressure of 15 to 25 Mpa is suitable from the standpoint of energy consumption amount and the corrosiveness of an apparatus. Namely, it is further preferable to comprise a process in which alcohol and/or water is allowed to co-exist with the above-mentioned fats and oils containing at least a fatty acid glyceride, and the reaction is conducted under conditions of a temperature of 200 to 300° C. and a pressure of 15 to 25 MPa, to convert a fatty acid glyceride and fatty acid contained in the above-mentioned fats and oils into a fatty acid alkyl ester. Under these reaction conditions, a fatty acid alkyl ester composition can be obtained particularly at high yield, and additionally, a fatty acid alkyl ester can be produced without using high temperature and high pressure conditions necessary in conventional supercritical methanol methods. Therefore, the energy consumption amount is small, additionally, there is no problem with safety and the corrosiveness of an apparatus, and there is no need to use an expensive special alloy such as hastelloy, inconel and the like for avoiding corrosion of an apparatus by fluid of high temperature and high pressure.

This first embodiment comprises a process in which a fatty acid glyceride and fatty acid contained in the above-mentioned fats and oils are converted into a fatty acid alkyl ester, and this process allows the reaction to be conducted in one step since it is inferred that by allowing alcohol and water to co-exist with raw material fats and oils containing at least a fatty acid glyceride, a fatty acid glyceride causes a hydrolysis reaction and/or transesterification and a fatty acid contained in fats and oils and/or a fatty acid produced by the above-mentioned hydrolysis reaction is converted into a fatty acid alkyl ester by an esterification reaction. In these reactions, alcohol and water, particular water, works as an acid catalyst under the conditions of reaction temperature and reaction pressure according to the present invention.

(Second Embodiment)

In the present invention, it is also preferable to comprise a first process of allowing water to co-exist with the above-mentioned fats and oils containing at least a fatty acid glyceride and conducting the reaction under conditions of a temperature of 100 to 370° C. and a pressure of 1 to 100 MPa, to convert the fatty acid glyceride contained in the above-mentioned fats and oils into a fatty acid, and a second process of adding alcohol to the product from the above-mentioned first process and further conducting the reaction under conditions of a temperature of 100 to 370° C. and a pressure of 5 to 100 MPa, to convert the fatty acid contained in the product from the first process into a fatty acid alkyl ester (second embodiment). Such a second embodiment is useful particularly since an unreacted fatty mono-glyceride, fatty di-glyceride and fatty tri-glyceride scarcely remain and are converted into a fatty acid in the first process and converted into a fatty acid alkyl ester effectively in the second process.

In the second embodiment, to conduct the reaction under reaction conditions of, particularly, a temperature of 150 to 300° C. and a pressure of 15 to 25 Mpa is suitable from the standpoint of the energy consumption amount and the corrosiveness of an apparatus. Namely, it is further preferable to comprise a first process of allowing water to co-exist with the above-mentioned fats and oils containing at least a fatty acid glyceride and conducting the reaction under conditions of a temperature of 150 to 300° C. and a pressure of 5 to 25 MPa, to convert the fatty acid glyceride contained in the above-mentioned fats and oils into a fatty acid, and a second process of adding alcohol to the product from the above-mentioned first process and further conducting the reaction under conditions of a temperature of 200 to 300° C. and a pressure of 15 to 25 MPa, to convert the fatty acid contained in the product from the first process into a fatty acid alkyl ester. These reaction conditions are particularly useful because of the same reason as in the case under the above-mentioned suitable reaction conditions in the first embodiment, namely, since a fatty acid alkyl ester composition can be obtained particularly at a high yield and additionally, there occurs no problem of high temperature and high pressure conditions necessary in conventional supercritical methanol methods.

In this second embodiment, the reaction is conducted in two steps comprising a first process of converting a fatty acid glyceride contained in the above-mentioned fats and oils and a second process of converting a fatty acid contained in the product from the first process into a fatty acid alkyl ester. Of them, the first process converts a fatty acid glyceride into a fatty acid by a hydrolysis reaction shown by the following reaction formula:

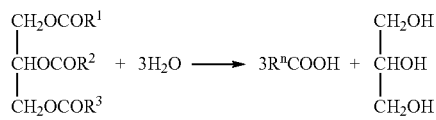

(wherein, n represents 1, 2 or 3, and R represents a saturated or unsaturated hydrocarbon group.).

As shown in the above-mentioned reaction formula, in the first process, a fatty acid glyceride in fats and oils used as a raw material is reacted with water, to produce a fatty acid ($R^n$COOH) liberated from the glyceride. This free fatty acid is subjected to the second process described later.

The above-mentioned reaction formula shows a fatty acid glyceride as an example, and additionally, when a fatty di-glyceride and/or fatty mono-glyceride are contained in fats and oils as a raw material, they are also hydrolyzed in the same manner.

In the second process, the free fatty acid produced in the hydrolysis reaction in the first process is, or, when a fatty acid is contained from the first in fats and oils as a raw material, this fatty acid and the above-mentioned free fatty acid are reacted with alcohol, to produce a fatty acid alkyl ester by an esterification reaction.

In the second process, esterification is conducted by thus reacting a fatty acid and alcohol. It has been clarified by the present inventors that the reaction speed of this esterification reaction is larger than the transesterification of conversion into a fatty ester by a reaction of a fatty acid glyceride and alcohol (see, FIG. 1). FIG. 1 is a graph showing a difference in the relation between the reaction time and the yield when an esterification reaction and transesterification are conducted at 300° C. and 30 Mpa.

Here, unreacted substances in the transesterification include mainly partial transesterified substances such as mono-glycerides and the like. This partial transesterified substance leads to an increase in the total glycerol amount causing an engine trouble when utilized in engine fuel oil. Therefore, it is inevitable to effect complete conversion into a fatty acid alkyl ester, however, a large amount of energy (longer reaction time) is necessary for this.

In the second embodiment of the present invention, it is particularly preferable that the first process is conducted at a temperature of 150 to 300° C., particularly 250 to 300° C. and a pressure of 5 to 25 MPa, particularly 15 to 25 MPa for 15 to 25 minutes, and the second process is conducted also at a temperature of 250 to 300° C. and a pressure of 15 to 25 MPa for 15 to 25 minutes.

(Third Embodiment)

The present invention also preferably comprises a process of allowing alcohol to co-exist with the above-mentioned fats and oils containing no fatty acid glyceride and conducting the reaction under conditions of a temperature of 100 to 370° C. and a pressure of 5 to 100 MPa (preferably, 5 to 50 MPa), to convert the fatty acid contained in the above-mentioned fats and oils into a fatty acid alkyl ester (third embodiment). Such a third embodiment is useful particularly since a fatty acid can be easily converted into a fatty acid alkyl ester which is impossible in an alkali metal catalytic method.

In the third embodiment, the reaction is suitably conducted at a temperature of 200 to 300° C. and a pressure of 15 to 25 Mpa. Namely, it is further preferable to comprise a process of allowing alcohol to co-exist with the above-mentioned fats and oils containing no fatty acid glyceride and conducting the reaction under conditions of a temperature of 200 to 300° C. and a pressure of 15 to 25 MPa, to convert the fatty acid contained in the above-mentioned fats and oils into a fatty acid alkyl ester. These reaction conditions are particularly useful because of the same reason as in the case under the above-mentioned suitable reaction conditions in the first embodiment, namely, since a fatty acid alkyl ester composition can be obtained particularly at high yield and additionally, there occurs no problem of high temperature and high pressure conditions necessary in conventional supercritical methanol methods.

This third embodiment comprises a process in which the above-mentioned fats and oils containing no fatty acid glyceride are used and the fatty acid contained in the fats and oils is converted into a fatty acid alkyl ester, and this is a simple process method since a fatty acid alkyl ester composition can be obtained only via the second process (esterification reaction) and without the first process (hydrolysis reaction) in the above-mentioned second embodiment.

In the production method of the present invention, when the above-mentioned fats and oils contain a fatty acid glyceride, it is preferable to use water in an amount of 3 to 1000 mol, particularly 30 to 400 mol per mol of the fatty acid glyceride from the standpoint of effectively progressing a hydrolysis reaction for conversion into a fatty acid, and it is preferable to use alcohol in an amount of 3 to 1000 mol, particularly 30 to 400 mol per mol of the fatty acid glyceride from the standpoint of effectively converting the fatty acid glyceride into a fatty acid alkyl ester directly by a transesterification, further, effectively converting the fatty acid produced by the above-mentioned hydrolysis reaction into a fatty acid alkyl ester.

When the above-mentioned fats and oils contain a fatty acid, it is preferable to use alcohol in an amount of 1 to 330 mol, particularly 10 to 130 mol per mol of the fatty acid from the standpoint of effectively converting the fatty acid into a fatty acid alkyl ester by an esterification reaction.

In the production method of the present invention, the reaction time is not particularly restricted provided the reaction is conducted within the above-mentioned range of the reaction temperature and reaction pressure, and the reaction time is appropriately set corresponding to the conditions of the reaction temperature and reaction pressure. In one example, when the reaction temperature is 250 to 300° C. and the reaction pressure is 15 to 30 MPa, for example, the reaction time is preferably 4 to 60 minutes, further preferably 30 to 50 minutes.

The raw material fats and oils used in the production method of the present invention include vegetable oils, animal oils and used waste oils thereof, and the like. The vegetable oils include natural vegetable fats and oils such as coconut oil, palm oil, palm kernel oil, soybean oil, rapeseed oil and the like. The animal oils include natural animal fats and oils such as beef tallow, lard, fish oil and the like. The waste oils include waste oils obtained after use of these vegetable oils and animal oils for a specific object. These fats and oils can be used singly or in admixture.

As the alcohol used in the production method of the present invention, alcohols having 1 to 10 carbon atoms are useful. It is preferable to use, particularly, lower alcohols having about 1 to 5 carbon atoms such as methyl alcohol, ethyl alcohol, propyl alcohol, i-propyl alcohol, butyl alcohol, 2-butyl alcohol, i-butyl alcohol, t-butyl alcohol, pentyl alcohol and the like, from the standpoint of producing a lower alkyl ester excellent as a diesel fuel oil, particularly, a bio-diesel fuel oil. Of them, particularly methyl alcohol is preferable since the cost thereof is low and recovery thereof is easy. Of course, higher alcohols having 6 or more carbon atoms such as decyl alcohol can also be used.

As the reaction apparatus used in the production method of the present invention, any apparatus can be used provided it can stand a high pressure and high temperature. When a hydrolysis reaction is conducted without a catalyst, alcohol and/or water works as an acid catalyst under the conditions according to the present invention.

The fatty acid alkyl ester composition obtained by the production method of the present invention can be used in various applications, and is particularly useful as a diesel fuel, among others, as a bio-diesel fuel.

The present invention will be illustrated further in detail by examples and comparative examples below. However, the scope of the invention is not at all limited to these examples.

EXAMPLE 1

Example According to the Second Embodiment of the Present Invention (First Case)

<1> First Process (Hydrolysis Reaction of Fatty Acid Glyceride)

1 ml of rapeseed oil (tri-glyceride content: 97.5%, free fatty acid content: 2.5%) and 4 ml of water (tri-glyceride/water=1/217 mol ratio) were filled in an Inconel-625 reaction tube having a content volume of 5 ml. This reaction tube was placed into a tin bath controlled at a predetermined temperature and reacted while shaking under a predetermined pressure for a predetermined time. After the predetermined reaction time, the reaction tube was quickly removed from the tin bath, and placed in a water bath and cooled quickly to room temperature. The content of the reaction tube was transferred into a measuring cylinder, and allowed to stand still for 30 minutes, to give two layers of an upper layer composed of the produced fatty acid (in some cases, containing an unreacted fatty acid glyceride) and a lower layer composed of water containing a glycerol. The upper layer was removed from this, and evaporated to completely remove water present in a trace amount.

<2> Second Process (Methyl-Esterification Reaction)

Next, into a reaction tube was added the fatty acid (in some cases, containing an unreacted fatty acid glyceride) obtained in the first process and about 4 ml of methanol (raw material tri-glyceride/methanol ratio=1/100 mol) to give a total amount of 5 ml, and a methyl-esterification reaction was conducted at a predetermined temperature under a predetermined pressure for a predetermined time. After predetermined reaction time, the reaction tube was cooled quickly to room temperature, and unreacted methanol and the produced water were removed from the content of the reaction tube. The resulting product was dissolved in fresh methanol, and the composition thereof was analyzed using a refractive index detector by high performance liquid chromatography (HPLC). From the composition analysis result, the yield of a methyl ester was obtained.

Conditions of the hydrolysis reactions in the examples (Examples 1-1 to 1-13) are shown in Table 1, and conditions of the methyl-esterification reaction are shown in Table 2, and the yields of fatty methyl esters obtained in the examples are shown together in Table 2.

TABLE 1

| | (Conditions of first process/hydrolysis reaction) | | | | |
|---|---|---|---|---|---|
| Example | Rapeseed oil (ml) | Water (ml) | Temperature (° C.) | Pressure (Mpa) | Reaction time (min) |
| Example 1-1 | 1.0 | 4.0 | 255 | 20 | 20 |

TABLE 1-continued (Conditions of first process/hydrolysis reaction)

| Example | Rapeseed oil (ml) | Water (ml) | Temperature (° C.) | Pressure (Mpa) | Reaction time (min) |
|---|---|---|---|---|---|
| Example 1-2 | 1.0 | 4.0 | 255 | 20 | 25 |
| Example 1-3 | 1.0 | 4.0 | 255 | 20 | 30 |
| Example 1-4 | 1.0 | 4.0 | 270 | 35 | 15 |
| Example 1-5 | 1.0 | 4.0 | 270 | 35 | 20 |
| Example 1-6 | 1.0 | 4.0 | 270 | 35 | 25 |
| Example 1-7 | 1.0 | 4.0 | 270 | 35 | 30 |
| Example 1-8 | 1.0 | 4.0 | 300 | 60 | 6 |
| Example 1-9 | 1.0 | 4.0 | 300 | 60 | 8 |
| Example 1-10 | 1.0 | 4.0 | 300 | 60 | 12 |
| Example 1-11 | 1.0 | 4.0 | 350 | 90 | 1 |
| Example 1-12 | 1.0 | 4.0 | 350 | 90 | 2 |
| Example 1-13 | 1.0 | 4.0 | 350 | 90 | 3 |

TABLE 2

(Conditions of second process/methyl-esterification reaction and yield of methyl ester)

| Example | Methanol (ml) | Temperature (° C.) | Pressure (Mpa) | Reaction time (min) | Yield* (%) |
|---|---|---|---|---|---|
| Example 1-1 | 4.0 | 255 | 19 | 20 | 78 |
| Example 1-2 | 4.0 | 255 | 19 | 25 | 93 |
| Example 1-3 | 4.0 | 255 | 19 | 30 | 98 |
| Example 1-4 | 4.0 | 270 | 25 | 15 | 89 |
| Example 1-5 | 4.0 | 270 | 25 | 20 | 98 |
| Example 1-6 | 4.0 | 270 | 25 | 25 | 98 |
| Example 1-7 | 4.0 | 270 | 25 | 30 | 98 |
| Example 1-8 | 4.0 | 300 | 30 | 6 | 81 |
| Example 1-9 | 4.0 | 300 | 30 | 8 | 90 |
| Example 1-10 | 4.0 | 300 | 30 | 12 | 96 |
| Example 1-11 | 4.0 | 350 | 43 | 2 | 60 |
| Example 1-12 | 4.0 | 350 | 43 | 3 | 82 |
| Example 1-13 | 4.0 | 350 | 43 | 4 | 97 |

*Yield: this shows a proportion against the theoretical value of a methyl-esterified compound when converted to 100% (also in the following examples)

EXAMPLE 2

Example According to the Second Embodiment of the Present Invention (Second Case)

<1> First Process (Hydrolysis Reaction of Fatty Acid Glyceride)

A hydrolysis reaction of a fatty acid glyceride was conducted according to the same operation procedure as in Example 1, excepting that the volume ratio of rapeseed oil (tri-glyceride content: 97.5%, free fatty acid content: 2.5%) and water was changed while keeping the reaction temperature and reaction time constant.

<2> Second Process (Methyl-Esterification Reaction)

Next, a methyl-esterification reaction was conducted according to the same operation procedure as in Example 1 excepting that a predetermined reaction temperature, reaction pressure and reaction time were applied.

The composition of the reaction product was analyzed by the same procedure as in Example 1, and from the analyzed result, the yield of a methyl ester was obtained.

Conditions of the hydrolysis reactions in the examples (Examples 2-1 to 2-6) are shown in Table 3, and conditions of the methyl-esterification reaction are shown in Table 4, and the yields of fatty methyl esters obtained in the examples are shown together in Table 4.

TABLE 3

(Conditions of first process/hydrolysis reaction)

| Example | Rapeseed oil (ml) | Water (ml) | Temperature (° C.) | Pressure (Mpa) | Reaction time (min) |
|---|---|---|---|---|---|
| Example 2-1 | 0.62 | 4.38 | 255 | 18 | 30 |
| Example 2-2 | 1.0 | 4.0 | 255 | 19 | 30 |
| Example 2-3 | 4.0 | 1.0 | 255 | 35 | 30 |
| Example 2-4 | 0.62 | 4.38 | 270 | 30 | 20 |
| Example 2-5 | 1.0 | 4.0 | 270 | 35 | 20 |
| Example 2-6 | 4.0 | 1.0 | 270 | 60 | 20 |

TABLE 4

(Conditions of second process/methyl-esterification reaction and yield of methyl ester)

| Example | Methanol (ml) | Temperature (° C.) | Pressure (Mpa) | Reaction time (min) | Yield (%) |
|---|---|---|---|---|---|
| Example 2-1 | 4.38 | 255 | 19 | 30 | 95 |
| Example 2-2 | 4.0 | 255 | 19 | 30 | 94 |
| Example 2-3 | 1.0 | 255 | 19 | 30 | 63 |
| Example 2-4 | 4.38 | 270 | 25 | 20 | 98 |
| Example 2-5 | 4.0 | 270 | 25 | 20 | 96 |
| Example 2-6 | 1.0 | 270 | 25 | 20 | 61 |

EXAMPLE 3

Example According to the Third Embodiment of the Present Invention (Esterification Reaction of Fatty Acid)

An esterification reaction of a fatty acid and methanol was conducted using, as a raw material, palmitic acid, stearic acid, oleic acid, linoleic acid and linolenic acid (all manufactured by Nacalai Tesque) commercially available as a reagent, and under conditions of volume ratio, temperature, pressure and reaction time shown in Table 5. For the esterification reaction of a fatty acid and methanol, a fatty acid and methanol were filled at a mole ratio of 1:42 in a Inconel-625 reaction tube having a content volume of 5 ml, and the same procedure as in the methyl-esterification reaction in Example 1 was conducted. After removal of unreacted methanol and produced water in the same manner as in Example 1, the reaction product was dissolved in fresh methanol and HPLC analysis was conducted. From the HPLC analysis result, the conversion from a fatty acid into a fatty acid alkyl ester (=yield of methyl ester) was obtained. The results are shown in Table 5 together with reaction conditions.

TABLE 5

| Example | Fatty acid | Fatty acid (ml)/ methanol (ml) | Temperature (° C.) | Pressure (Mpa) | Reaction time (min) | Yield (%) |
|---|---|---|---|---|---|---|
| Example 3-1 | $C_{16-0}$ | 0.91:4.09 | 270 | 17 | 20 | 90 |
| Example 3-2 | $C_{16-0}$ | 0.91:4.09 | 300 | 24 | 7 | 88 |
| Example 3-3 | $C_{16-0}$ | 0.91:4.09 | 350 | 43 | 4 | 75 |
| Comparative example 3-1 | $C_{16-0}$ | 0.91:4.09 | 400 | 75 | 2 | 92 |
| Example 3-4 | $C_{18-0}$ | 0.91:4.09 | 270 | 17 | 20 | 98 |
| Example 3-5 | $C_{18-0}$ | 0.91:4.09 | 300 | 24 | 7 | 98 |
| Example 3-6 | $C_{18-0}$ | 0.91:4.09 | 350 | 43 | 4 | 100 |
| Comparative example 3-2 | $C_{18-0}$ | 0.91:4.09 | 400 | 75 | 2 | 100 |
| Example 3-7 | $C_{18-1}$ | 0.91:4.09 | 270 | 17 | 20 | 98 |
| Example 3-8 | $C_{18-1}$ | 0.91:4.09 | 300 | 24 | 7 | 98 |
| Example 3-9 | $C_{18-1}$ | 0.91:4.09 | 350 | 43 | 4 | 98 |
| Comparative example 3-3 | $C_{18-1}$ | 0.91:4.09 | 400 | 75 | 2 | 94 |
| Example 3-10 | $C_{18-2}$ | 0.91:4.09 | 270 | 17 | 20 | 98 |
| Example 3-11 | $C_{18-2}$ | 0.91:4.09 | 300 | 24 | 7 | 98 |
| Example 3-12 | $C_{18-2}$ | 0.91:4.09 | 350 | 43 | 4 | 87 |
| Comparative example 3-4 | $C_{18-2}$ | 0.91:4.09 | 400 | 75 | 2 | 80 |
| Example 3-13 | $C_{18-3}$ | 0.91:4.09 | 270 | 17 | 20 | 99 |
| Example 3-14 | $C_{18-3}$ | 0.91:4.09 | 300 | 24 | 7 | 96 |
| Example 3-15 | $C_{18-3}$ | 0.91:4.09 | 350 | 43 | 4 | 93 |
| Comparative example 3-5 | $C_{18-3}$ | 0.91:4.09 | 400 | 75 | 2 | 61 |

$C_{16-0}$: palmitic acid,
$C_{18-0}$: stearic acid,
$C_{18-1}$: oleic acid,
$C_{18-2}$: linoleic acid,
$C_{18-3}$: linolenic acid

EXAMPLE 4

Example According to the First Embodiment of the Present Invention (Hydrolysis of Tri-Glyceride and Esterification of Fatty Acid: 1-Step Reaction)

Reaction of Fats and Oils Containing a Free Fatty Acid and Tri-Glyceride, and Water and Methanol 1.6 ml of rapeseed oil (tri-glyceride content: 97.5%, free fatty acid content: 2.5%), a predetermined amount of water and predetermined amount of methanol were filled in an Inconel-625 reaction tube having a content volume of 5 ml. This reaction tube was placed into a tin bath controlled at predetermined temperature and reacted while shaking under a predetermined pressure for 4 minutes. After the reaction, the reaction tube was quickly removed from the tin bath, and placed in a water bath and cooled quickly to room temperature. Unreacted methanol and water and by-product of glycerin were removed from the content of the reaction product. The composition of the resulting product was analyzed in the same manner as in Example 1, and from the composition analysis result, the yield of a methyl ester was obtained.

Reaction conditions in examples (Examples 4-1 to 4-8) are shown in Table 6, and the yields of fatty methyl esters obtained in the examples are shown together in Table 6.

TABLE 6

| Example | Fat and oil (ml) | Water (ml) | Methanol (ml) | Temperature (° C.) | Pressure (Mpa) | Reaction time (min) | Yield (%) |
|---|---|---|---|---|---|---|---|
| Example 4-1 | 1.6 | 0.05 | 3.35 | 350 | 43 | 4 | 98 |
| Example 4-2 | 1.6 | 0.1 | 3.3 | 350 | 43 | 4 | 97 |
| Example 4-3 | 1.6 | 0.2 | 3.2 | 350 | 45 | 4 | 98 |
| Example 4-4 | 1.6 | 0.3 | 3.1 | 350 | 46 | 4 | 98 |
| Example 4-5 | 1.6 | 0.4 | 3.0 | 350 | 46 | 4 | 97 |
| Example 4-6 | 1.6 | 0.5 | 2.9 | 350 | 48 | 4 | 95 |
| Example 4-7 | 1.6 | 0.8 | 2.6 | 350 | 50 | 4 | 95 |
| Example 4-8 | 1.6 | 1.6 | 1.8 | 350 | 50 | 4 | 94 |
| Example 4-9 | 1.6 | 0.05 | 3.35 | 300 | 26 | 10 | 91 |
| Example 4-10 | 1.6 | 0.1 | 3.3 | 300 | 27 | 10 | 91 |
| Example 4-11 | 1.6 | 0.5 | 2.9 | 300 | 27 | 10 | 92 |
| Example 4-12 | 1.6 | 0.8 | 2.6 | 300 | 28 | 10 | 92 |

TABLE 6-continued

| Example | Fat and oil (ml) | Water (ml) | Methanol (ml) | Temperature (° C.) | Pressure (Mpa) | Reaction time (min) | Yield (%) |
|---|---|---|---|---|---|---|---|
| Example 4-13 | 1.6 | 1.6 | 1.8 | 300 | 28 | 10 | 92 |
| Example 4-14 | 1.6 | 0.8 | 2.6 | 270 | 18 | 40 | 94 |
| Example 4-15 | 1.6 | 1.6 | 1.8 | 270 | 19 | 40 | 94 |

The fatty acid alkyl ester composition obtained in each example of Examples 1 to 4 could be confirmed to be useful as a bio-diesel fuel oil.

EXAMPLE 5

Esterification Reaction and Transesterification of Fatty Acid

An esterification reaction of a fatty acid and alcohol or a transesterification of rapeseed oil and alcohol was conducted using, as a raw material, fats and oils and alcohols shown in Table 7, under conditions of mole ratio, temperature, pressure and reaction time shown in Table 7. Since about 98.5% of rapeseed oil is composed of a tri-glyceride, the reaction from rapeseed oil can be judged to be a transesterification.

The reaction product was subjected to HPLC analysis in the same manner as in Example 1, from the HPLC analysis result, conversion into a fatty acid alkyl ester from a fatty acid or rapeseed oil (=yield of alkyl ester) was obtained. The results are shown in Table 7 together with the reaction conditions.

TABLE 7

| Example | Alcohol/fats and oils (mole ratio) | Fats and oils | Alcohol | Temperature (° C.) | Pressure (Mpa) | Reaction time (min) | Yield (%) |
|---|---|---|---|---|---|---|---|
| Example 5-1 | 42/1 | $C_{18-3}$ | Methanol | 300 | 20 | 8 | 96.2 |
| Example 5-2 | 42/1 | $C_{18-2}$ | | 300 | 20 | 8 | 95.1 |
| Example 5-3 | 42/1 | $C_{18-1}$ | | 300 | 20 | 8 | 95.8 |
| Example 5-4 | 42/1 | $C_{18-0}$ | | 300 | 20 | 8 | 94.7 |
| Example 5-5 | 42/1 | $C_{16-0}$ | | 300 | 20 | 8 | 94.0 |
| Example 5-6 | 42/1 | Rapeseed oil | | 300 | 20 | 15 | 98.0 |
| Example 5-7 | 42/1 | Rapeseed oil | | 350 | 43 | 4 | 98.0 |
| Example 5-8 | 42/1 | $C_{18-3}$ | Ethanol | 300 | 15 | 12 | 94.6 |
| Example 5-9 | 42/1 | $C_{18-2}$ | | 300 | 15 | 14 | 97.4 |
| Example 5-10 | 42/1 | $C_{18-1}$ | | 300 | 15 | 14 | 95.9 |
| Example 5-11 | 42/1 | $C_{18-0}$ | | 300 | 15 | 15 | 91.2 |
| Example 5-12 | 42/1 | $C_{16-0}$ | | 300 | 15 | 14 | 91.7 |
| Example 5-13 | 42/1 | Rapeseed oil | | 300 | 15 | 45 | 96.7 |
| Example 5-14 | 42/1 | Rapeseed oil | | 350 | 25 | 10 | 97.1 |
| Example 5-15 | 42/1 | $C_{18-3}$ | 1-propanol | 300 | 10 | 15 | 97.0 |
| Example 5-16 | 42/1 | $C_{18-2}$ | | 300 | 10 | 14 | 92.7 |
| Example 5-17 | 42/1 | $C_{18-1}$ | | 300 | 10 | 14 | 92.3 |
| Example 5-18 | 42/1 | $C_{18-0}$ | | 300 | 10 | 14 | 89.6 |
| Example 5-19 | 42/1 | $C_{16-0}$ | | 300 | 10 | 14 | 90.1 |
| Example 5-20 | 42/1 | Rapeseed oil | | 300 | 10 | 45 | 96.1 |
| Example 5-21 | 42/1 | Rapeseed oil | | 350 | 23 | 14 | 98.8 |
| Example 5-22 | 42/1 | $C_{18-3}$ | 1-butonal | 300 | 9 | 15 | 97.3 |

TABLE 7-continued

| Example | Alcohol/fats and oils (mole ratio) | Fats and oils | Alcohol | Temperature (° C.) | Pressure (Mpa) | Reaction time (min) | Yield (%) |
|---|---|---|---|---|---|---|---|
| Example 5-23 | 42/1 | $C_{18-2}$ | | 300 | 9 | 14 | 92.4 |
| Example 5-24 | 42/1 | $C_{18-1}$ | | 300 | 9 | 14 | 86.1 |
| Example 5-25 | 42/1 | $C_{18-0}$ | | 300 | 9 | 14 | 82.5 |
| Example 5-26 | 42/1 | $C_{16-0}$ | | 300 | 9 | 14 | 81.1 |
| Example 5-27 | 42/1 | Rapeseed oil | | 300 | 9 | 45 | 87.1 |
| Example 5-28 | 42/1 | Rapeseed oil | | 350 | 23 | 14 | 95.3 |
| Example 5-29 | 42/1 | Rapeseed oil | 1-octanol | 300 | 6 | 45 | 68.7 |
| Example 5-30 | 42/1 | Rapeseed oil | | 350 | 19 | 20 | 90.7 |

$C_{16-0}$: palmitic acid,
$C_{18-0}$: stearic acid,
$C_{18-1}$: oleic acid,
$C_{18-2}$: linoleic acid,
$C_{18-3}$: linolenic acid From the results shown in Table 7, the following matters are evident.

In the transesterification using rapeseed oil as a raw material of fats and oils (reaction temperature: 300° C.), the treatment time is 15 minutes and the yield is about 98% in a reaction with methanol, on the other hand the treatment time is 45 minutes and the yield is about 87% in a reaction with butanol. Further, it is found, in this transesterification, that when the number of carbon atoms in alcohol decreases, its reactivity increases (see FIG. 2, for the above-mentioned matters). Even in the same transesterification at a reaction temperature of 350° C., the same matter is applied (see, FIG. 3). In this example, a batch type apparatus was used, however, it is also possible to use a flow type apparatus which shows no influence of pressure, namely, which can effect treatment under the same pressure condition (described later). For reference, the critical temperature and critical pressure of various alcohols used in the examples are shown in Table 8 together with the temperature and pressure conditions in the examples.

TABLE 8

| Alcohol | Critical temperature (° C.) | Critical pressure (Mpa) | Pressure in example (MPa) | |
|---|---|---|---|---|
| | | | 300° C. | 350° C. |
| Methanol | 239 | 8.09 | 20 | 43 |
| Ethanol | 243 | 6.38 | 15 | 25 |
| 1-propanol | 264 | 5.06 | 10 | 23 |
| 1-butanol | 287 | 4.90 | 9 | 23 |
| 1-octanol | 385 | 2.86 | 6 | 19 |

Figure 6:
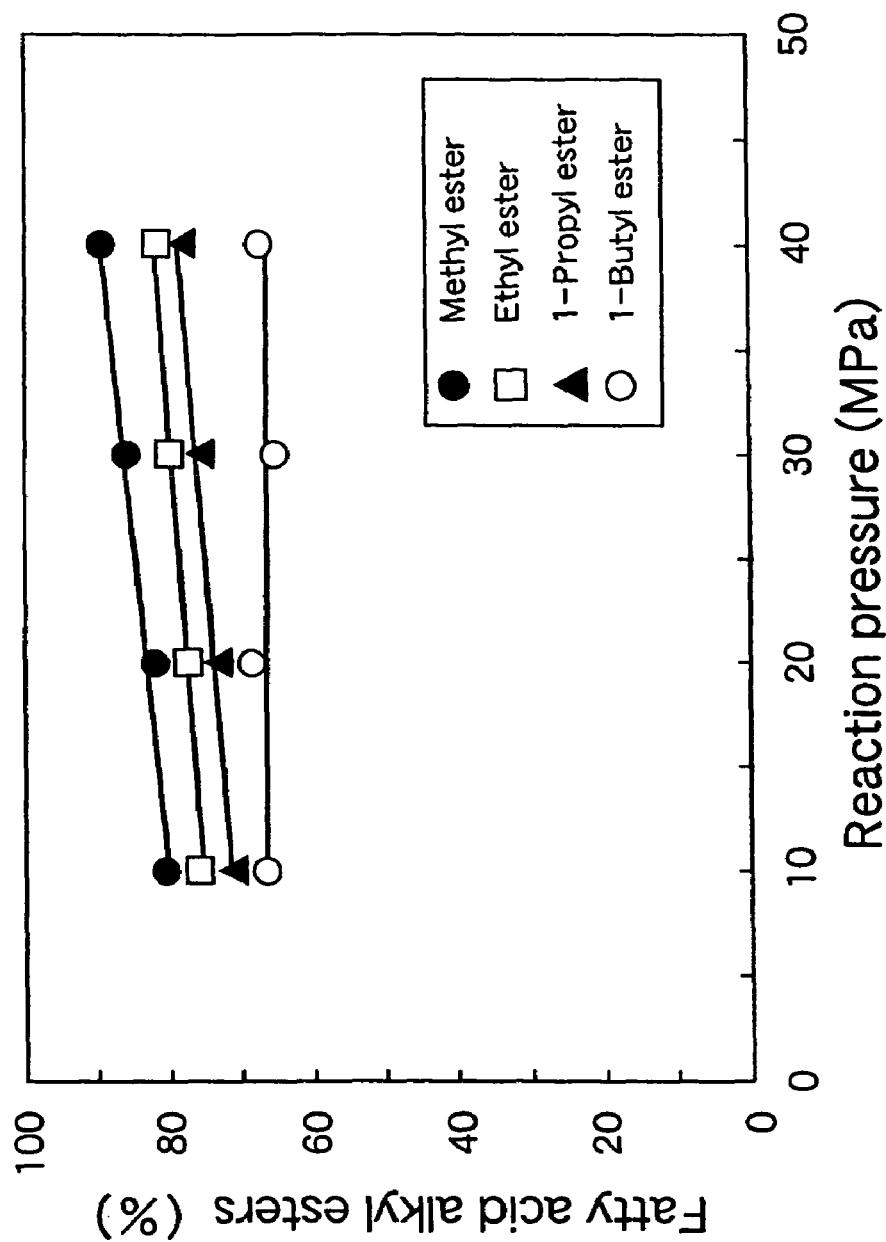
FIG. 6 is a graph showing the relation between the pressure and the yield of a fatty acid alkyl ester composition at 300° C. under the same pressure for 20 minutes by a flow type apparatus.

As shown in Table 8, when a batch type apparatus is used and if the number of carbon atoms of alcohol is higher, pressure in the reaction tube decreases, and resultantly, there is a possibility of a decrease also in the yield of a fatty acid alkyl ester. On the other hand, when a reaction is conducted using a flow type apparatus under the same condition, results shown in a graph of FIG. 6 are obtained. That is, it becomes evident that even if compared under the same pressure condition, if the number of carbon atoms of alcohol is higher, yield also decreases, and a conclusion is obtained that a flow type apparatus gives the same result as that of a batch type apparatus.

Esterification reactions when various fatty acids are used as a raw material of fats and oils show little difference in reactivity depending on the kind of alcohol and fatty acid, and the reactions are completed in a treatment time of about 15 minutes (see, FIG. 4).

From the above-mentioned results, it is clear that a method by an esterification reaction has higher reactivity as compared with a method by a transesterification.

Figure 5:
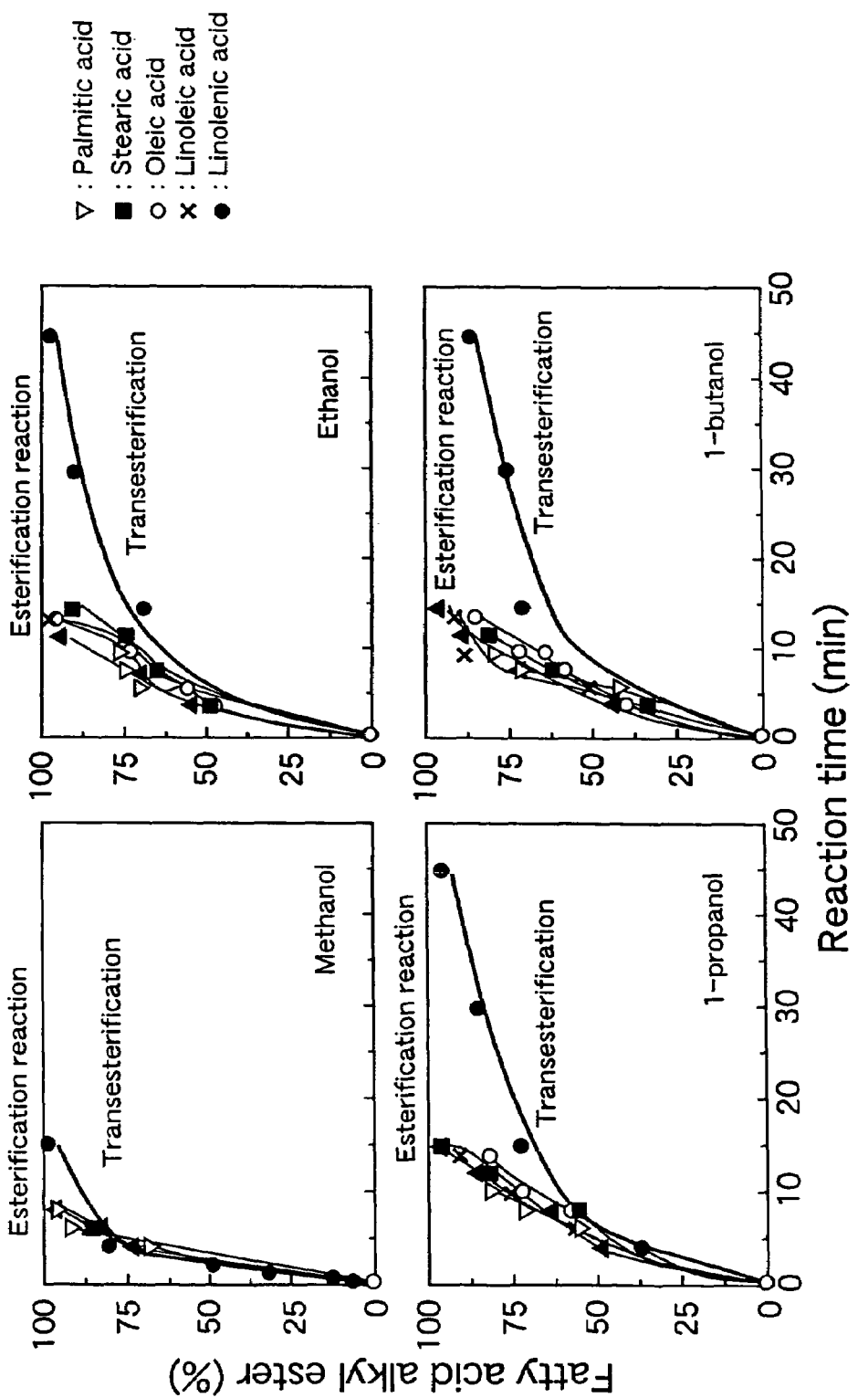
FIG. 5 provides graphs showing a difference in the relation between the reaction time of a transesterification of rapeseed oil and an esterification reaction of various fatty acids by various supercritical alcohol treatments at 300° C. and the yield of the produced various fatty acid alkyl ester compositions.

Since the condition of reaction pressure varies between various alcohols, a mutual comparison of them is difficult, however, the reaction of each alcohol is conducted under the conditions of the same pressure and the same temperature By this, it is clear that a reaction (esterification reaction) using various fatty acids as a raw material of fats and oils gives faster alkyl-esterification as compared with a reaction (transesterification) using rapeseed oil (see FIG. 5).

Therefore, a reaction can be completed in a shorter time, namely, energy can be saved, when a tri-glyceride is hydrolyzed to give a fatty acid, then, the fatty acid is alkyesterified.

The fatty acid alkyl ester composition obtained in each example of Example 5 can be confirmed to be useful as a bio-diesel fuel oil.

Industrial Applicability

The present invention can solve a problem of separation and recovery of catalysts present in an alkali metal catalytic method, a problem of excess consumption of a catalyst by a free fatty acid in a raw material, and a problem of a decrease in transesterification due to water in a raw material, and further, solves a problem of the presence of a large excess amount of alcohol in a conventional supercritical methanol method, and can produce a fatty acid alkyl ester composition without being influenced in the progress of a reaction even water and free fatty acid contained in the reaction system.

What is claimed is:

1. A method for producing a fatty acid alkyl ester composition using fates and oils containing a fatty acid glyceride and/or fatty acid, wherein alcohol and/or water is present along with said fats and oils in a same reaction vessel and the reaction is conducted under conditions of a temperature of 100° C. to 370° C. and a pressure of 1 to 100 MPa, wherein the amount of water is 3 to 1000 mol per mol of the fatty acid glyceride contained in said fats and oils, and the amount of alcohol is 1 to 330 mol per mol of the fatty acid contained in said fats and oils.

2. The method for producing a fatty acid alkyl ester composition according to claim 1, wherein alcohol and water is present in said same reaction vessel along with said fats and oils, and said fats and oils contain a fatty acid glyceride, and conducting the reaction under conditions of a temperature of 100° C. to 370° C. and a pressure of 5 to 100 MPa, to convert the fatty acid glyceride and fatty acid contained in said fats and oils into a fatty alkyl ester.

3. The method for producing a fatty acid alkyl ester composition according to claim 1, comprising a first step wherein water is present along with said fats and oils containing at least a fatty acid glyceride in said same reaction vessel and said reaction is conducted under conditions of a temperature of 100° C. to 370° C. and a pressure of 1 to 100 MPa, to convert the fatty acid glyceride contained in said fats and oils into fatty acid, and a second step wherein alcohol is added to the product from said first step and a reaction is conducted under conditions of a temperature of 100° C. to 370° C. and a pressure of to 100 MPa, to convert the fatty acid contained in the product from the process into a fatty acid alkyl ester.

4. The method for producing a fatty acid alkyl ester composition according to claim 1, comprising a process wherein alcohol is present with said fats and oils in said vessel and said fats and oils contain no fatty acid glyceride and conducting the reaction under conditions of a temperature of 100° C. to 370° C. and a pressure to 5 to 100 MPa, to convert the fatty acid contained in said fats and oils into a fatty acid alkyl ester.

5. The method for producing a fatty acid alkyl ester composition according to claim 1, wherein the amount of water is 30 to 400 mol and the amount of alcohol is 30 to 400 mol per mol of the fatty acid glyceride contained in said fats and oils, and the amount of alcohol is 10 to 130 mol per mol of the fatty acid contained in said fats and oils.

6. The method for producing a fatty acid alkyl ester composition according to claim 1, using alcohol having 1 to 10 carbon atoms as said alcohol.

7. The method for producing a fatty acid alkyl ester composition according claim 1, wherein said fatty acid alkyl ester composition is used as a diesel fuel oil.

8. The method for producing a fatty acid alkyl ester composition according to claim 1, wherein said reaction is conducted in the absence of a metal alkali catalyst and an acid catalyst.

9. The method for producing a fatty acid alkyl ester composition according to claim 1, wherein said reaction is conducted in the absence of any catalyst.

* * * * *